(12) United States Patent
Berger et al.

(10) Patent No.: US 8,741,622 B2
(45) Date of Patent: Jun. 3, 2014

(54) STRESS TOLERANT BIFIDOBACTERIA

(71) Applicant: Nestec S.A., Vevey (CH)

(72) Inventors: Bernard Berger, Chatillens (CH); Enea Rezzonico, Epalinges (CH); Fabrizio Arigoni, Geneva (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/847,787

(22) Filed: Mar. 20, 2013

(65) Prior Publication Data

US 2013/0273660 A1    Oct. 17, 2013

Related U.S. Application Data

(62) Division of application No. 12/739,099, filed as application No. PCT/EP2008/008898 on Oct. 22, 2008, now Pat. No. 8,426,190.

(30) Foreign Application Priority Data

Oct. 23, 2007  (EP) .................................... 07119097

(51) Int. Cl.
    *C12N 1/00*    (2006.01)
(52) U.S. Cl.
    USPC ...................................................... 435/252.1
(58) Field of Classification Search
    None
    See application file for complete search history.

(56) References Cited

FOREIGN PATENT DOCUMENTS

WO    WO0077186    12/2000

OTHER PUBLICATIONS

F. Guarner et al., "Probiotics," Int. J. Food Microbiology, No. 39, pp. 237-238, 1998.
P. Simpson et al., "Intrinsic tolerance of *Bifidobacterium* species to heat and oxygen and survival following spray drying and storage," J. App. Microbiol., No. 99, pp. 493-501, 2005.
K. Hokamp, et al., "ArrayPipe: a flexible processing pipeline for microarray data," Nucleic Acids Research, vol. 32, Feb. 2004, Web Server Issue W457-W459.
G. Schmidt, et al., Basic features of the stress response in three species of bifidobacteria: *B. longum. B. adolscentis*, and *B. breve*, International Journal of Food Microbiology, vol. 55 (2000), pp. 41-45, XP000964630.
M. Ventura, "The clpB gene of *Bifidobacterium breve* UCC 2003: transcriptional analysis and first insights into stress induction," Microbiology, vol. 51, (2005), pp. 2861-2872, XP002488436.
M. Ventura, et al., "How high G+C Gram-positive bacteria and in particular bifidobacteria cope with heat stress: protein players and regulators," FEMS Microbiology Reviews, Sep. 2006, vol. 30, No. 5, pp. 734-759, XP002488437.
E. Rezzonico, et al., "Global transcriptome analysis of the heat shock response of *Bifidobacterium longum*," FEMS Microbiology Letters, Jun. 2007, vol. 271, No. 1, pp. 136-145, XP002488438.
International Search Report for International Application No. PCT/EP2008/008898 mailed on Mar. 3, 2009.
Written Opinion for International Application No. PCT/EP2008/008898 mailed on Mar. 3, 2009.

*Primary Examiner* — Allison Ford
*Assistant Examiner* — Yvonne Pyla
(74) *Attorney, Agent, or Firm* — K&L Gates LLP

(57) ABSTRACT

The present invention relates in general to the field of Bifidobacteria. In particular, the present invention relates to the field of Bifidobacteria with a modulated stress resistance. One embodiment of the present invention is a *Bifidobacterium* with a constitutively modulated DnaK, GrpE and/or ClpB expression.

11 Claims, 6 Drawing Sheets

FIG. 2
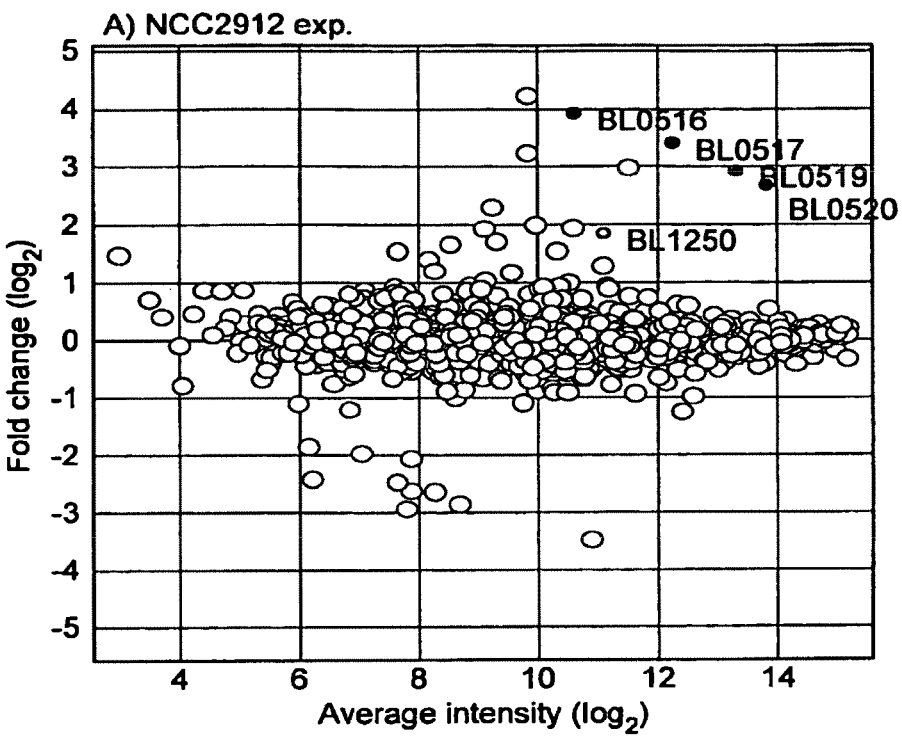
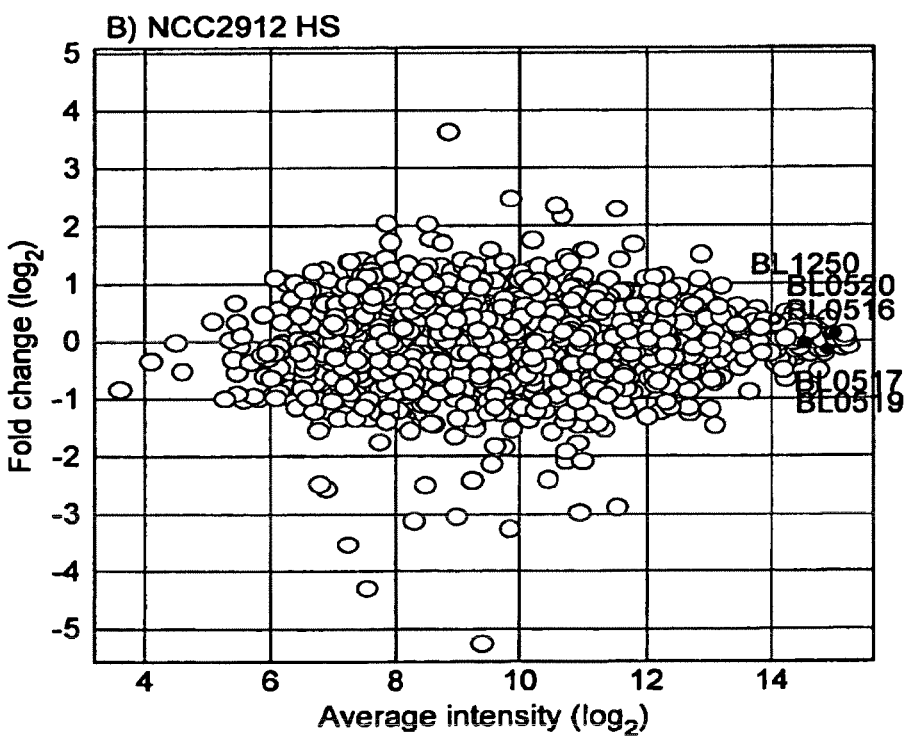

FIG. 2 CONT'D
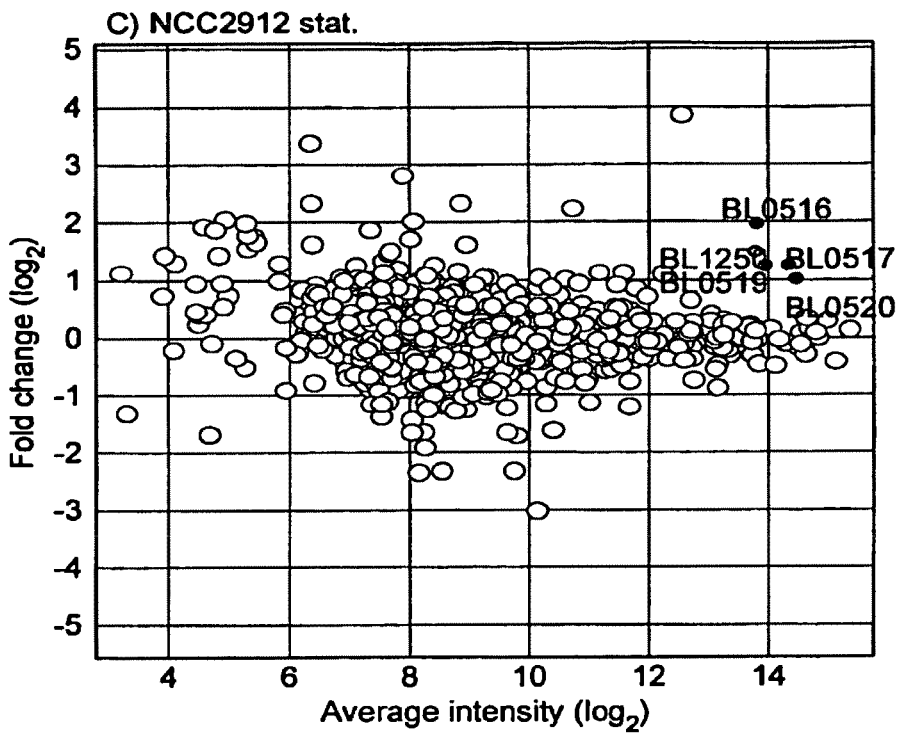
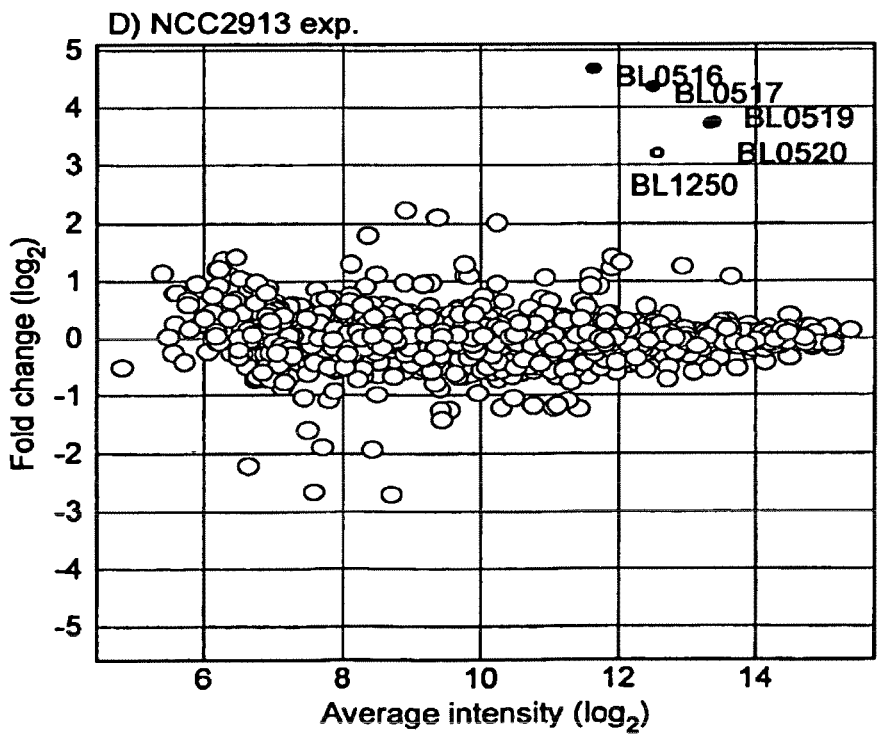

FIG. 2 CONT'D
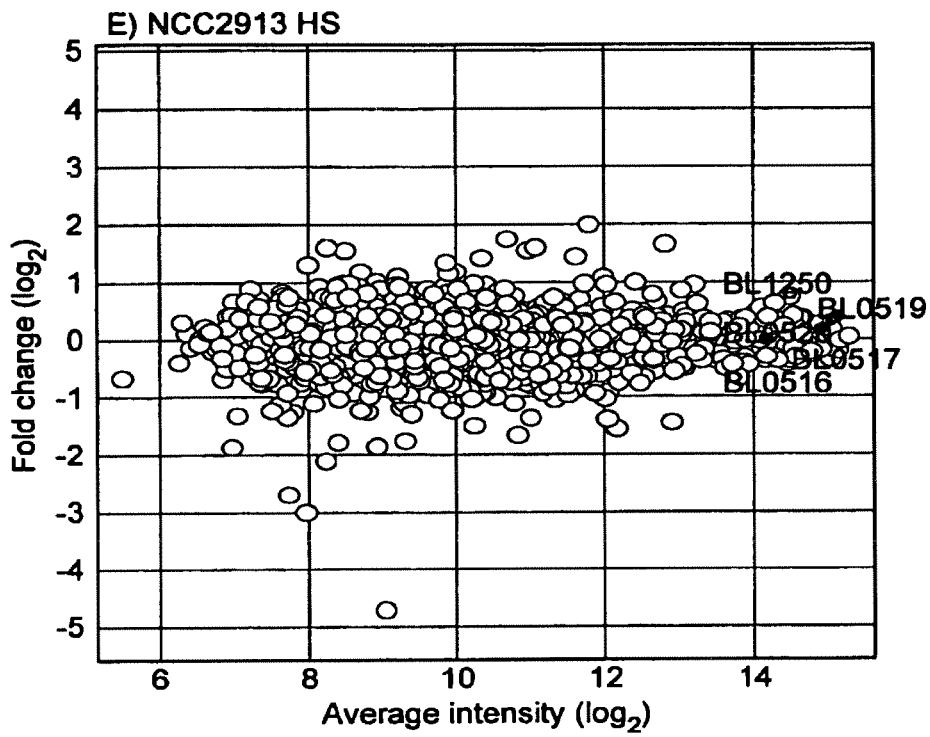
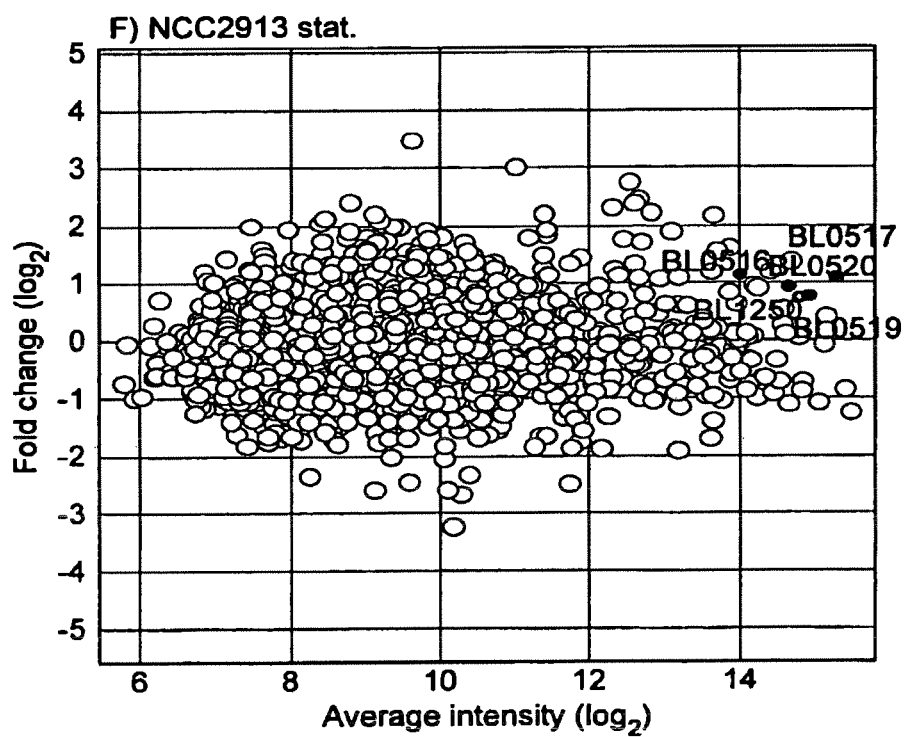

Viability log loss after 13 min 59°C HS

| Complement: | no | no | hspR-wt | hspR-Mut1 |
| Strain: | wt | Mut1 | | |

Viability log loss after 13 min 59°C HS

| Complement: | no | Empty vector | hspR-wt |
| Strain: | wt | | |

STRESS TOLERANT BIFIDOBACTERIA

PRIORITY CLAIM

This application is a divisional of U.S. application Ser. No. 12/739,099, filed Apr. 21, 2010, which is a National Stage of International Application No. PCT/EP2008/008898, filed on Oct. 22, 2008 which claims priority to European Patent Application No. 07119097.9, filed on Oct. 23, 2007, the entire contents of which are incorporated herein by reference.

FIELD

The present invention relates in general to the field of Bifidobacteria. In particular the present invention relates to the field of Bifidobacteria with a modulated stress resistance.

SEQUENCE LISTING

This disclosure includes a sequence listing submitted as a text file pursuant to 37 C.F.R. §1.52(e)(v) named CI-#9372442-v1-3712036_1800_ST25.TXT, created on Jun. 18, 2013, with a size of 2,620 bytes, which is incorporated herein by reference. The attached sequence descriptions and Sequence Listing comply with the rules governing nucleotide and/or amino acid sequence disclosures in patent applications as set forth in 37 C.F.R. §§1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. §1.822.

BACKGROUND

Probiotic bacteria are selected for their health-promoting properties. As probiotics exert their benefit as living organism (Guarner, F. and G. J. Schaafsma. 1998. "Probiotics". Int. J. Food Microbiol. 39:237-238), the bacteria should survive the gastro-intestinal track conditions. In industrial application, large-scale production requires the additional ability of the probiotics to tolerate food processing and storage. These production steps are characterized by different stresses compromising the good survival of the bacteria. Amongst them, high or low temperature, high osmotic pressure, oxidation, and humidity are likely key factors.

Some species of probiotic bacteria are in particular known to have a poor temperature, oxygen, or spray-drying tolerance. Prominent examples of such probiotics with a poor stress tolerance are, e.g., Bifidobacteria, in particular *Bifidobacterium longum* (Simpson, P. J., C. Stanton, G. F. Fitzgerald, and R. P. Ross. 2005. "Intrinsic tolerance of *Bifidobacterium* species to heat and oxygen and survival following spray drying and storage". J. Appl. Microbiol. 99:493-501).

To address this problem and to increase the survival rate of probiotics during food production, several approaches are presently used, including microencapsulation, addition of protective agents, oxygen-impermeable packaging, and improvement of the growth or processing conditions.

However, these approaches are complex and laborious to carry out and often require the addition of further compounds that may have side effects and that may be unwanted in the final food-product.

On the other hand there are applications where it is desired to have as few living bacteria in a product as possible. Presently, such sterile products are prepared by applying intense heat and/or pressure. In this case it would be desirable to have probiotics available that can effectively be inactivated even without the need for high energy treatments.

SUMMARY

To overcome these problems of the prior art the present inventors have chosen a different approach to modulate, in particular increase or decrease the number of living probiotic bacteria, in particular of Bifidobacteria, in a product. The present inventors have searched for naturally occurring Bifidobacteria strains with a modulated stress resistance.

Consequently, it was the object of the present invention to provide the art with probiotic Bifidobacteria, that exhibit a modulated, in particular an increased or a decreased stress resistance and with a method to modulate, in particular increase or decrease, the number of viable probiotics in a food or pharmaceutical product.

BRIEF DESCRIPTION OF THE DRAWINGS

Further examples and features of the present invention are apparent from the following examples and figures.

FIG. 2 shows the global analysis of their transcriptome by microarrays that we performed. In all three strains we found that the dnaK operon and the clpB gene were overexpressed (data not shown for NCC2923). The expression levels of each gene are expressed versus the expression level of the wt *B. longum* strain NCC2705, in exponential growth phase (A and D), in exponential phase after a 7-minute heat-shock (B and E), and in stationary phase (C and F). Genes of the dnaK operon are shown in black (BL0516=hspR, BL0517=dnaJ, BL0519=grpE, and BL0520=dnaK), clpB (=BL1250) in white. The other genes are depicted in grey.

DETAILED DESCRIPTION

Figure 1:
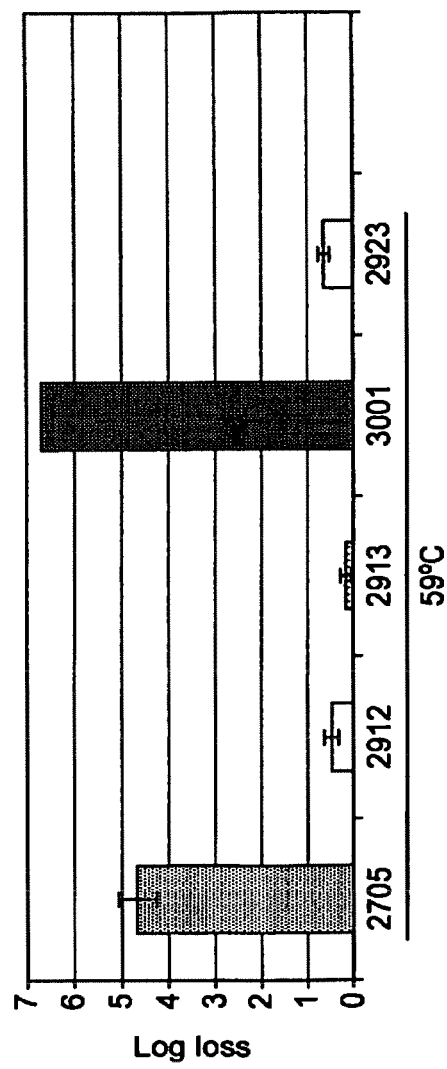
FIG. 1 shows that the new *B. longum* isolates NCC2912, NCC2913 and NCC2923 are significantly more resistant to heat-shock. Error bars show the confidence interval from 3 to 15 replicates (P=0.05); *, beyond detection limit.

This object of the present invention is solved by a *Bifidobacterium* in accordance with claim 1, by a composition in accordance with claim 10, by a use in accordance with claim 13 and by a method in accordance with claim 15.

In particular the inventors were surprised to find that a *Bifidobacterium* with a constitutively modulated DnaK, DnaJ, GrpE and/or ClpB expression solves the object of the present invention.

The inventors found that it is surprisingly possible to regulate the stress resistance of Bifidobacteria by modulating DnaK, DnaJ, GrpE and/or ClpB expression constitutively. In particular constitutively upregulating the DnaK, DnaJ, GrpE and/or ClpB expression will result in an increased stress resistance while constitutively downregulating the DnaK, DnaJ, GrpE and/or ClpB expression will result in a reduced stress resistance.

Consequently, one preferred embodiment of the present invention is a *Bifidobacterium* wherein the DnaK, DnaJ, GrpE and/or ClpB expression is constitutively upregulated. An improved stress resistance has several advantages. The probiotic effectiveness of Bifidobacteria can be increased if the bacteria are administered alive and even more if they are able to arrive alive in the intestine, so that they can reach the intestine and exert their effect. Stress resistant Bifidobacteria are more likely to survive stress causing treatments, as it is the case, for example, in the production of food or medicaments. Stress resistant Bifidobacteria are also more likely to survive conditions in the human body on their way to the intestine.

It may also be desired to have available Bifidobacteria with reduced stress resistance, e.g., in cases where a complete inactivation of bacteria is wanted prior to administration. This has the advantage that the effect of Bifidobacteria can exactly be custom fitted, since a multiplication of effectiveness by colonization can be excluded. Less stress resistant Bifidobacteria may also be desired in sterile compositions or for laboratory or production purposes.

If the DnaK, DnaJ, GrpE and/or ClpB expression is modulated, generally any degree of modulation that causes an effect on the stress resistance of Bifidobacteria is envisaged and within the scope of the present invention.

However, preferably in case of upregulation, the *Bifidobacterium* in accordance with the present invention may exhibit a DnaK, DnaJ, GrpE and/or ClpB expression that is about 1.5-100 fold upregulated, compared to a *Bifidobacterium* under standard conditions.

Standard conditions are defined as follows: Culture in anaerobiosis at 37° C. in MRS medium (Becton Dickinson AG, Basel, Switzerland; 10 g casein peptone, 10 g meat extract, 5 g yeast extract, 20 g glucose, 1 g tween 80, 2 g $K_2HPO_4$, 5 g Na-acetate, 2 g $(NH_4)_2$ citrate, 0.2 g $MgSO_4 \times 7 H_2O$, 0.05 g $MnSO_4 \times H2O$, 1 liter distilled water, pH adjusted to 6.2-6.5) containing 0.05% (wt/vol) cysteine. Cells may be in exponential growth phase ($OD_{600\,mm}$ of 0.7) or in stationary phase.

Generally a protein expression is "upregulated" or a protein is "over-expressed" when it is expressed or produced in an amount or yield that is higher than a given base-line yield that occurs in nature at standard conditions.

Over-expression of a protein can be achieved, for example, by altering any one or more of: (a) the growth or living conditions of the host cells; (b) the polynucleotide encoding regulator polypeptides; (c) the promoter used to control expression of the polynucleotide and its copy number in the cell; and (d) the host cells themselves.

Likewise, a protein expression is "down-regulated" or a protein is "under-expressed" when it is produced in an amount or yield that is lower than the amount or yield of a protein than a given base-line yield that occurs in nature at standard conditions.

In this context, the expression level or yield refers to the amount or concentration of protein that is expressed, or protein that is produced (i. e. expression product), whether or not in an active or functional form.

A preferred embodiment of the present invention is a *Bifidobacterium*, wherein the DnaK, DnaJ, GrpE and/or CipB expression is upregulated to about the same level as a wild-type *Bifidobacterium* after a heat shock, in particular in mid exponential phase.

A heat shock for gene expression measurements is defined as follows: Bacteria anaerobically grown in MRS medium (Becton Dickinson AG, Basel, Switzerland, see above for composition) containing 0.05% (wt/vol) cysteine at 37° C. are harvested in mid exponential phase ($OD_{600\,mm}$ of 0.7). Then, a 200 ml aliquot is centrifuged, and the pellets suspended. in 90 ml of 50° C. prewarmed MRS-cys medium. The concentrated bacterial suspension is incubated 7 minutes at 50° C. A 10 ml sample is then collected, centrifuged, and the pellet immediately frozen in liquid nitrogen before gene expression measurement.

This will ensure that the upregulation of DnaK, DnaJ, GrpE and/or CipB expression corresponds to a level that the Bifidobacteria can reach by external stimulation. Importantly, the increased level of DnaK, DnaJ, GrpE and/or CipB expression will correspond to a level that can be reached naturally, so that an overexpression beyond natural levels which might turn out to be toxic for the cell is avoided.

The modulation of DnaK, DnaJ, GrpE and/or ClpB expression in the *Bifidobacterium* in accordance with the present invention may be achieved by a modulated HspR expression and/or HspR functioning.

Without wishing to be bound by theory the present inventors believe that HspR might regulate the DnaK, DnaJ, GrpE and/or ClpB expression in the *Bifidobacterium*. The modulation of DnaK, DnaJ, GrpE and/or ClpB expression by modulating HspR expression and/or HspR functioning has the advantage that by influencing the expression level and/or the functioning of one molecule the expression of DnaK, DnaJ, GrpE and ClpB can be regulated simultaneously. Expression control by the negative regulator HspR might be increased or decreased, depending on the fact whether a down- or upregulated DnaK, DnaJ, GrpE and/or ClpB expression is required. Generally, reducing the concentration of HspR will result in an upregulation of DnaK, DnaJ, GrpE and/or ClpB expression and, consequently, in improved stress resistance. Similarly a less functional HspR will result in an upregulation of DnaK, DnaJ, GrpE and/or ClpB expression and in improved stress resistance.

If the stress resistance is to be decreased, HspR-control may be tightened by increasing its cellular concentration (increased expression) and/or by increasing its functioning.

HspR functioning and/or expression can be influenced by any method that is known to those skilled in the art.

For example, the *Bifidobacterium* in accordance with the present invention might comprise at least one mutation that modulates HspR expression and/or HspR functioning. This at least one mutation may be located within the hspR gene.

It is preferred that the at least one mutation is located within the coding sequence of the hspR gene. The mutation may be any kind of mutation that is known to those skilled in the art. Any kind of sequence alteration of a gene is considered a mutation. Preferably, the mutation is selected from the group consisting of point mutations, in particular missense mutations and nonsense mutations, insertions and deletions.

In a preferred embodiment of the present invention the Bi>rdobacterium comprises at least one point mutation in the hspR gene. The term "point mutation" as used herein means a nucleic acid substitution and/or deletion. Alternatively or simultaneously, the at least one mutation may at least partially hinder HspR expression and/or HspR functioning.

A "coding sequence" is a nucleotide sequence that, when expressed, results in the production of a protein, i.e., the nucleotide sequence encodes an amino acid sequence for that protein. Preferably, the coding sequence is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence may be "under the control" of transcriptional and translational control sequences in a cell.

The term "gene" means a DNA sequence that codes for or corresponds to a particular sequence of amino acids which comprise all or part of one or more proteins, and may or may not include regulatory DNA sequences, such as promoter sequences, which determine for example the conditions under which the gene is expressed.

If the mutation is located within the coding sequence of the DnaK, DnaJ, GrpE, ClpB and/or HspR gene it is preferred that this mutation alters the functioning of the protein. Mutations within the coding sequence may serve to improve or to decrease the functioning of the protein.

If the mutation is located within the regulatory DNA sequences of the DnaK, DnaJ, GrpE, ClpB and/or HspR gene, e.g., in the transcriptional and translational control sequences, it is preferred that this mutation modulates the expression of the protein. Mutations within the regulatory DNA sequences may serve to upregulate or to downregulate the expression of the protein.

A regulatory DNA sequence comprises transcriptional or translational control sequences, such as, e.g., a promoter, enhancer, terminator, that provide for the expression of a coding sequence in a host cell.

A transcriptional or translational control sequence comprises e.g., a transcription factor, that induces, up-regulates, down-regulates, or affects, the transcription or translation, respectively, of a gene.

A "promoter" is a DNA regulatory region capable of binding RNA polymerase in a cell and initiating transcription of a downstream (3'direction) coding sequence.

The *Bifidobacterium* in accordance with the present invention may be. selected from the group consisting of *Bifidobacterium adolescentis, Bifidobacterium angulatum, Bifidobacterium animalis, Bifidobacterium asteroids, Bifidobacterium bifidum, Bifidobacterium bourn, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacterium indicum, Bifidobacterium infantis, Bifidobacterium inopinatum, Bifidobacterium lactis, Bifidobacterium longum, Bifidobacterium magnum, Bifidobacterium merycicum, Bifidobacterium minimum, Bifidobacterium pseudocatenulatum, Bifidobacterium pseudolongum, Bifidobacterium pullorum, Bifidobacterium ruminantium, Bifidobacterium saeculare, Bifidobacterium subtile, Bifidobacterium suis, Bifidobacterium thermacidophilum* and *Bifidobacterium thermophilum*.

Preferably, the *Bifidobacterium* is a *Bifidobacterium longum*.

Through natural selection the present inventors were able to provide the strains *Bifidobacterium longum* NCC2912, *Bifidobacterium longum* NCC2913, and *Bifidobacterium longum* NCC2923 as particular preferred embodiments of the present invention. The strains have been deposited under the Budapest treaty with the CNCM; Institut Pasteur, 25; Rue du Docteur Roux; F-75724 Paris Cedex 15. NCC2912 was deposited as CNCM 1-3853, NCC2913 was deposited as CNCM 13854 and NCC2923 was deposited as CNCM 1-3855. Strains obtained by natural selection have the advantage that they solve the object of the present invention without having been modified by means of gene technology.

The present invention also comprises a composition comprising the *Bifidobacterium* of the present invention. The composition may be any composition but preferably is a medicament or a food product.

Bifidobacteria, when administered, confer a health benefit on the host. The health benefits of Bifidobacteria are manifold and include aid in digestion, association with a lower incidence of allergies, prevention of some forms of tumour growth and weight management.

Preferably, the medicament or food product is intended for humans, pets or livestock, while pets or livestock may be selected from the group consisting of dogs, cats, guinea pigs, rabbits, pigs, cattle, sheep, goats, horses and/or poultry.

The composition may be a nutritional composition comprising at least one carbohydrate source, at least one lipid source and/or at least one protein source.

As protein source any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The proteins may be intact or hydrolysed or a mixture of intact and hydrolysed proteins. it may be desirable to supply partially hydrolysed proteins (degree of hydrolysis between 2 and 20%), for example for animals believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil.

The source of carbohydrates preferably provides 40% to 80% of the energy of the composition. Any suitable carbohydrate may be used, for example sucrose, lactose, glucose, fructose, corn syrup solids, maltodextrins, and mixtures thereof.

Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyllactose and oligosaccharides derived from animal milks. A preferred fibre blend is a mixture of inulin with shorter chain fructooligosaccharides. Preferably, if fibre is present, the fibre content is between 2 and 40 g/l of the composition as consumed, more preferably between 4 and 10 g/l.

The composition may also contain minerals and micronutrients such as trace elements and vitamins in accordance with the recommendations of Government bodies such as the USRDA. For example, the composition may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 μg iodine, 5 to 15 μg selenium, 1000 to 3000 μg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 μg Vitamin B12, 100 to 800 μg folic acid, 30 to 70 μg biotin, 1 to 5 pg Vitamin D, 3 to 10 μg Vitamin E.

One or more food grade emulsifiers may be incorporated into the composition if desired; for example diacetyl tartaric acid esters of mono- and di-glycerides, lecithin and mono- and di-glycerides. Similarly suitable salts and stabilisers may be included.

The composition may be intended for oral, parenteral or topical administration. Oral application includes for the purpose of the present invention enteral administration.

The composition may comprise at least one other kind of other food grade bacteria. "Food grade bacteria" means bacteria that are used and generally regarded as safe for use in food. The food grade bacteria may be selected from the group consisting of lactic acid bacteria, probiotic bacteria and/or bifidobacteria. "Probiotic bacteria" mean microbial cell preparations or components of microbial cells with a beneficial effect on the health or well-being of the host. (Salminen 8, Ouwehand A. Benno Y. et al "Probiotics: how should they be defined" Trends Food Sci. Technol. 1999:10 107-10). The composition may further contain at least one prebiotic. "Prebiotic" means food substances intended to promote the growth of probiotic bacteria in the intestines. The prebiotic may be selected from the group consisting of oligosaccharides and optionally contains fructose, galactose, mannose, soy and/or inulin; and/or dietary fibers.

The composition of the present invention may further contain protective hydrocolloids (such as gums, proteins, modified starches), binders, film forming agents, encapsulating agents/materials, wall/shell materials, matrix. compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The composition of the present invention may contain any number of Bifidobacteria in accordance with the present invention. In principle, a single *Bifidobacterium* that arrives in the intestine and is able to generate a colony is sufficient to generate a beneficial effect on the host.

If the composition is a medicament it typically may comprise between $10^3$ and $10^{10}$ cfu of at least one *Bifidobacterium* in accordance with the present invention per daily dose. If the composition is a medicament it may also comprise between $10^3$ and $10^{10}$ cells of at least one *Bifidobacterium* in accordance with the present invention per daily dose.

If the composition is a food product it typically may comprise between $10^3$ and $10^{12}$ cfu of at least one *Bifidobacterium* in accordance with the present invention per g of the dry weight of the food composition. If the composition is a food product it may also comprise between $10^3$ and $10^{12}$ cells of at least one *Bifidobacterium* in accordance with the present invention per g of the dry weight of the food composition.

The present invention also relates to the use of a *Bifidobacterium* in accordance with the present invention to increase the number of living probiotic bacteria, in particular living Bifidobacteria, in a product. Similarly, the present invention relates to the use of the composition of the present invention to increase the number of living probiotic bacteria in a product. Finally the present invention also relates to the use of a *Bifidobacterium* in accordance with the present invention to prepare a composition of the present invention to increase the number of living probiotic bacteria, in particular living Bifidobacteria, in a product.

The uses of the present invention serve also to increase the number of probiotic bacteria, in particular of Bifidobacteria, in a product after exposure to stress for the probiotic bacteria.

Stress may be selected from the group consisting of an exposure to heat of about 40-120° C. for 30 seconds to 2 hours, temperature changes, mechanical stress, or long term storage, low moisture storage and/or freeze drying or spray drying.

Temperature changes may be at least two subsequent variations in temperature with an amplitude of more than 5° C. within 2 hours in the temperature range of −80° C.+120° C.

Long term storage is storage for more than 1 week, preferably more than 1 month even more preferred more than 6 months, with a water activity up to 0.33 and at a temperature in the range from 25° C. to 45° C.

Finally, the present invention relates to a method to increase the stress resistance of a *Bifidobacterium* comprising the step constitutively upregulating the DnaK, DnaJ, GrpE and/or ClpB expression, in particular by introducing at least on point mutation in the hspR gene of the *Bifidobactenum*, so that HspR expression and/or HspR functioning is hindered.

It is clear to those of skill in the art that they can freely combine any features of the present invention described herein without departing from the scope of the invention as disclosed.

EXAMPLES

Example 1

Isolation of Bifidobacteria of the Present Invention

The new *B. longum* isolates were obtained by successive natural selection of heat resistant mutants of the original wt strains. Each cycle of selection consisted of applying a 13 min heat-shock (HS) stress to 5 ml of O/N (overnight) culture in MRS medium (Becton Dickinson AG, Basel, Switzerland) containing 0.05% (wt/vol) cysteine (MSR-cys). HS were performed by successive dilution of the culture. The culture was 10× diluted in 45 ml of preheated medium and placed in a heated water-bath. Similarly, the temperature was rapidly decreased by diluting the 50 ml with 225 ml of medium at RT. The resulting culture was grown 16 h in anaerobiosis (AnaeroGen, Oxoid AG, Basel, Switzerland) at 37° C. (until stationary phase) before being submitted to a new cycle of selection. Finally, after around 25 cycles, clones were isolated by double streaking to generate pure cultures from colonies obtained after HS.

A similar approach was applied to select for natural mutants showing an increased resistance to oxygen. For this cyclic selection, bacterial populations were plated on MRS agar surface in the presence of controlled concentrations of oxygen: After a pre-incubation period of 4-5 h in anaerobiosis, the agar plates were incubated in jars flushed with a mixture of air and pure nitrogen. In parallel, cells were also grown anaerobically, as a reference. The colonies from the aerobic incubation were collected, grown anaerobically in MRS-cyst liquid media and subjected to the next cycle of oxidative stress. The concentration of the oxygen treatment was increased each time that the cell count of the oxygen treated plates equals the cell count of the anaerobic reference. Finally, clones were isolated. We obtained new *B. longum* strains growing on MRS agar plates under 15% oxygen pressure without loss of survival.

Example 2

Heat-Shock Resistance of NCC2912, NCC2913 and NCC2923

NCC2912, NCC2913, NCC2923, NCC2705 and NCC3001 were tested for their heat shock resistance. NCC2705 and NCC3001 are wt *B. longum* strains used as reference The heat shock was carried out as follows: 1.5 ml of an ON culture was diluted in 135 ml of pre-warmed MRS medium (Becton Dickinson AG, Basel, Switzerland, see above for composition) containing 0.05% (wt/vol) cysteine, incubated 13 min, then 100 µl were cooled down in a dilution microtiter plate. During the selection process and for the HS assays, cell counts were performed before and after HS. Plates were incubated 48 h at 37° C. before counting. The viability loss is expressed in log after dividing the post-HS count by the pre-HS count.

FIG. 1 gives the viability loss (in log) after a 13-minute heat-shock at 59° C. It shows that the new *B. longum* isolates NCC2912, NCC2913 and NCC2923 are significantly more resistant to heat-shock.

Example 3

Analysis of the Transcriptome of the Heat Resistant Strains

The global analysis of the transcriptome of the heat resistant bacterial strains by microarrays was performed as follows. Bacteria were grown in MRS medium (Becton Dickinson AG, Basel, Switzerland, see above for composition) containing 0.05% (wt/vol) cysteine at 37° C. Precultures were incubated in anaerobic conditions, whereas cultures for heat shock experiment were grown in 0.5 liter Sixfors fermenters (Infors AG, Bottmingen, Switzerland) with stirring (150 rpm) under $CO_2$ atmosphere. All fermentations were performed in duplicate. In mid exponential phase ($OD_{600\ nm}$ of 0.7) bacterial cultures were sampled before HS, 25 ml being centrifuged at RT for 5 min at 3600 g. Then, the pellet was immediately frozen in liquid nitrogen and stored at −80° C. In parallel, a 200 ml aliquot was centrifuged, and the pellets suspended in 90 ml of 50° C. prewarmed MRS-cys medium. The concentrated bacterial suspension was incubated 7 minutes at 50° C. A 10 ml sample was collected, centrifuged, and the pellet was immediately frozen in liquid nitrogen For stationary phase sampling, the $OD_{600\ nm}$ of batch cultures performed in 10 ml tubes was monitored until the stationary phase was reached (16 h). The cells were then harvested as described above. RNA extraction and quality check were performed as previously described (Rezzonico, E., S. Lariani, C. Barretto, G. Cuanoud, G. Giliberti, M. Delley, F. Arigoni, and G. Pessi. 2007. "Global transcriptome analysis of the heat shock response of *Bifidobacterium longum*". FEMS Microbiol. Lett. 271:136-145) except for an additional DNaseI treatment (Ambion) performed before using the RNeasy kit (Qiagen). Agilent 60-mer oligo microarrays were designed with 4 to 5 probes per gene (Agilent technologies Inc., USA). RNA labelling and cDNA synthesis were carried out using the 3DNA Array 900 MPX Genisphere kit (Genisphere Inc., Hatfield, Pa., USA) combined with the In situ Hybridization Kit Plus. The hybridization conditions and the washing of the slide were performed as follows. To the 20 µl of cDNA (obtained with the Genisphere kit), 25 µl of control target Agilent, 60 µl of $H_2O$ and 105 µl of Agilent buffer were added. After 10 minutes of incubation at 80° C. and 15 minutes at 65° C., the reaction was loaded on a pre-warmed slide in the hybridization chamber and incubated for 16 hours at 65° C., at four rpm in an Agilent oven. The cDNA hybridization was washed 10 min at 42° C. in 6×SSC, 0.005% Triton x-100 and 10 min at RT in 0.2×SSC, 0.00016% Triton x-100. The 3DNA hybridization was carried out as described in the Genisphere protocol except for the hybridization volume which was increased to 204 µl and the washing was modified as follows 10 min at 65° C. in 2×SSC, 0.0016% Triton x-100, 5 min at RT in 2×SSC, 0.0016% Triton x-100 and 10 min at RT in 0.2×SSC, 0.00016% Triton x-100. The slides were scanned at 10 µm with a Scanarray 4000 (Packard Biochip Technologies, Billerica, Mass., USA) and the data extracted with Imagene 5.6 (Biodiscovery, El Segundo, Calif., USA). Data were treated with homemade scripts in Python language (www.python.org) and a local installation of the ArrayPipe web server (Hokamp, K., F. M. Roche, M. Acab, M. E. Rousseau, B. Kuo, D. Goode, D. Aeschliman, J. Bryan, L. A. Babiuk, R. E. Hancock, and F. S. Brinkman. 2004. ArrayPipe: a flexible processing pipeline for microarray data. Nucleic Acids Res. 32:W457-W459). Probes showing a signal smaller than twice the standard deviation of the local background were considered without signal. Probes showing no signal or saturated signals in both channels were discarded from the analysis. Assuming an intensity-dependent variation in dye signal, (limma) loess global normalization was applied on signal ratios. Having several probes per gene, we summarized the results for each gene as follows. Within each hybridization data set, the gene fold change was given by the median of the corresponding probes values. Average intensity was calculated based on the same "selected" probes. Between hybridizations, the gene values are given by the mean of the gene values obtained from each hybridization.

FIG. 2 shows the results of the global transcriptome analysis. In all three strains we found that the dnaK operon and the clpB gene were overexpressed (data not shown for NCC2923). The expression levels of each gene are expressed versus the expression level of the wt B. Ion gum strain NCC2705, in exponential growth phase (A and D), in exponential phase after a 7-minute heat-shock (B and E), and in stationary phase (C and F). Genes of the dnaK operon are shown in black (BL0516=hspR, BL0517=dnaJ, BL0519=grpE, and BL0520=dnaK), clpB (=BL1250) in white. The other genes are depicted in grey.

Example 4

Sequencing of Stress Resistant Strains

Figure 3:
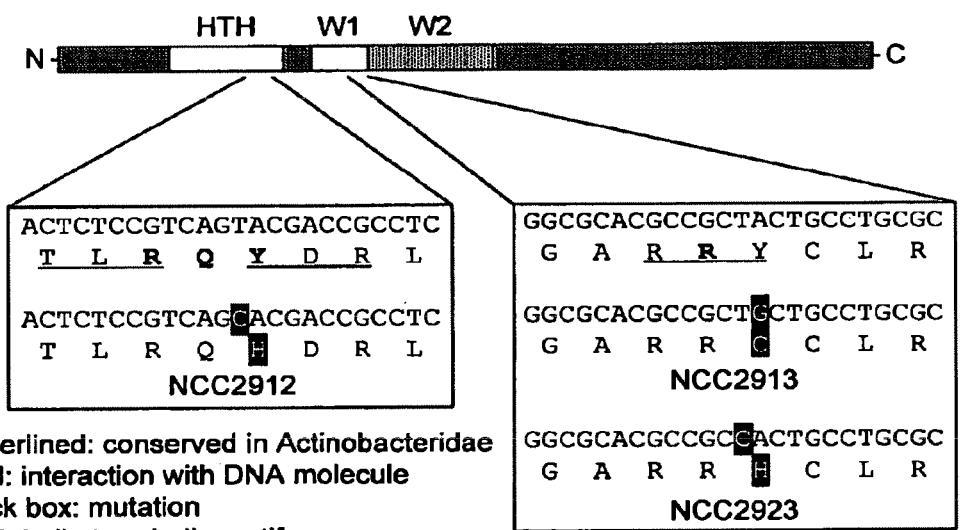
FIG. 3 shows the point mutations that were discovered when the hspR gene coding for the negative regulator of dnaK and clpB was sequenced. In black boxes, mutations in the new *B. longum* strains; underlined, residues conserved in Actinobacteridae; bold, residues for which interaction with DNA molecules were observed in this family of regulators; HTH, helix-turn-helix motif; W1 and W2, winged helix motif.

The hspR gene of the stress resistant strains NCC2912, NCC2913, NCC2923 was sequenced in an attempt to identify the molecular reason for their remarkable stress resistance and for the over-expression of the dnaK operon and the clpB gene. Sequencing was performed by Fastens SA (Geneva). FIG. 3 shows the point mutations that were discovered when the hspR gene coding for the negative regulator of dnaK and c/pB was sequenced. These point mutations affect protein domains likely responsible for the binding of the regulators to the promoter DNA. In white, mutations in the new *B. longum* strains; underlined, residues conserved in Actinobacteridae; bold, residues for which interaction with DNA molecules were observed in this family of regulators; HTH, helix-turn-helix motif; W1 and W2, winged helix motif.

Example 5

Complementation Experiments

Figure 4:
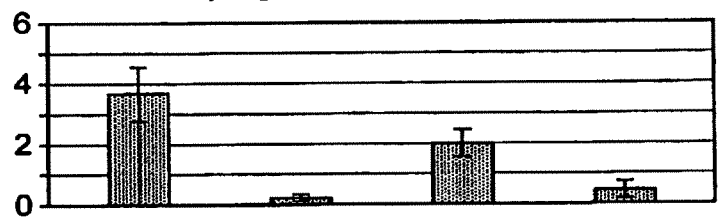
FIG. 4 shows results that demonstrate (for NCC2912) that these mutations were responsible for the observed heat-tolerance phenotype. Complementation of the mutant strains by the wt regulator HspR restores its heat-sensitivity. The figure shows the viability loss after a 13-minute heat-shock at 59° C. and the effect of the complementation of the heat-tolerant strain by the wt hspR gene. Mut1=NCC2912; wt=NCC2705; error bars show the standard deviation from 3 replicates.

We demonstrated by gene complementation that the mutations in the hspR gene were responsible for the observed heat-tolerance phenotype. Results are depicted in FIG. 4. Complementation of the mutant strains by the wt regulator HspR restores its heat-sensitivity. The complementation was performed as follows. The hspR gene of NCC2705 was amplified from genomic DNA with Expand High Fidelity PCR System (Roche, Germany) and the two primers CCCGGGCTCGAGATGGCGCGGTTAGCCAACC (SEQ ID NO: 1) and CCCGGGAAGCTTTCACCAACCCCA-CAGGACC (SEQ ID NO: 2). The 600 by amplicon was cloned into the XhoI and HindIII sites of the pGUSA plasmid. The DNA sequences were verified by sequencing (Fasteris, Geneva). Plasmids were transformed into NCC2912. DNA manipulations, plasmid isolation, transformation of *E. coli* and *B. longum* were performed as previously described (Klijn, A., D. Moine, M. Delley, A. Mercenier, F. Arigoni, and R. D. Pridmore. 2006. "Construction of a reporter vector for the analysis of *Bifidobacterium longum* promoters". Appl. Environ. Microbiol. 72:7401-7405). Plasmid pGUSA is described in this latter reference. The figure shows the viability loss after a 13-minute heat-shock at 59° C. and the effect of the complementation of the heat-tolerant strain by the wt hspR gene. Mut1=NCC2912; wt=NCC2705; error bars show the standard deviation from 3 replicates.

Example 6

Over-Expression of the HspR Regulator in the wt Strain Confers an Increased Heat-Sensitivity to the wt Strain Similarly to example 5, we over-expressed the wt HspR regulator of NCC2705 in the wt strain NCC2705 and showed that the constitutive over-expression of the HspR regulator in the wt strain confers an increased heat-sensitivity to the wt strain.

Figure 5:
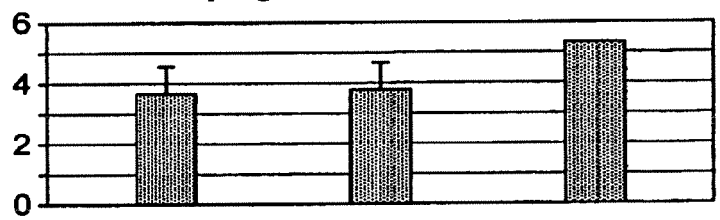
FIG. 5 shows that the constitutive over-expression of the HspR regulator in the wt strain confers an increased heat-sensitivity to the wt strain. The figure shows the viability loss after a 13-minute heat-shock at 59° C. and the effect of the complementation of the wt strain by the wt hspR gene. wt=NCC2705; error bars show the standard deviation from 3 replicates; *, beyond detection limit.

Results are depicted in FIG. 5, which shows the viability loss after a 13-minute heat-shock at 59° C. wt=NCC2705.

---

The invention is claimed as follows:

1. A method for increasing the number of living probiotic bacteria in a product comprising the steps of producing the product using *Bifidobacterium* with a constitutively modulated expression of a gene selected from the group consisting of DnaK, DnaJ, GrpE, ClpB and combinations thereof, and the *Bifidobacterium* is selected from the group consisting of *Bifidobacterium longum* NCC2912, *Bifidobacterium longum* NCC2913, *Bifidobacterium longum* NCC2923 and combinations thereof.

2. The method of claim 1, wherein the expression is upregulated.

3. The method of claim 2, wherein the expression is about 1.5-100 fold upregulated, compared to a *Bifidobacterium* under standard conditions.

4. The method of claim 2, wherein the expression is upregulated to a level that is about the same as a wild-type *Bifidobacterium* after a heat shock.

5. The method of claim 1, wherein the *Bifidobacterium* has a mutation in the hspR gene that modulates a characteristic selected from the group consisting of HspR expression, HspR functioning and a combination thereof.

6. The method of claim 1, wherein the *Bifidobacterium* has a mutation in the hspR gene that at least partially hinders a characteristic selected from the group consisting of HspR expression, HspR functioning and a combination thereof.

7. The method of claim 1, wherein the *Bifidobacterium* has a point mutation in the hspR gene.

8. The method of claim 7, wherein the hspR gene comprises a DNA sequence selected from the group consisting of SEQ ID NO: 3, 5, 7, 9 and 11.

9. The method of claim 1, wherein the *Bifidobacterium* is exposed to a stress selected from the group consisting of heat of about 40-120° C. for 30 seconds to 2 hours, temperature changes, mechanical stress, long term storage, low moisture storage, spray drying and combinations thereof.

10. The method of claim 1, wherein the *Bifidobacterium* has a mutation located within the hspR gene.

11. The method of claim 1, wherein the *Bifidobacterium* is *Bifidobacterium longum* NCC2913.

* * * * *

SEQUENCE LISTING

```
<160> NUMBER OF SEQ ID NOS: 12

<210> SEQ ID NO 1
<211> LENGTH: 31
<212> TYPE: DNA
<213> ORGANISM: Artificial sequence
<220> FEATURE:
<223> OTHER INFORMATION: Synthesized: hspR primer 1

<400> SEQUENCE: 1
cccgggctcg agatggcgcg gttagccaac c                              31

<210> SEQ ID NO 2
<211> LENGTH: 31
<212> TYPE: DNA
<213> ORGANISM: Artificial sequence
<220> FEATURE:
<223> OTHER INFORMATION: Synthesized: hspR primer 2

<400> SEQUENCE: 2
cccgggaagc tttcaccaac cccacaggac c                              31

<210> SEQ ID NO 3
<211> LENGTH: 24
<212> TYPE: DNA
<213> ORGANISM: Artificial sequence
<220> FEATURE:
<223> OTHER INFORMATION: Synthesized: hspR mutation 1

<400> SEQUENCE: 3
actctccgtc agtacgaccg cctc                                      24

<210> SEQ ID NO 4
<211> LENGTH: 8
<212> TYPE: PRT
```

```
<213> ORGANISM: Artificial sequence
<220> FEATURE:
<223> OTHER INFORMATION: Synthesized: hspR mutation 1

<400> SEQUENCE: 4

Thr Leu Arg Gln Tyr Asp Arg Leu
1               5

<210> SEQ ID NO 5
<211> LENGTH: 24
<212> TYPE: DNA
<213> ORGANISM: Artificial sequence
<220> FEATURE:
<223> OTHER INFORMATION: Synthesized: hspR mutation 2

<400> SEQUENCE: 5
actctccgtc agcacgaccg cctc                                            24

<210> SEQ ID NO 6
<211> LENGTH: 8
<212> TYPE: PRT
<213> ORGANISM: Artificial sequence
<220> FEATURE:
<223> OTHER INFORMATION: Synthesized: hspR mutation 2

<400> SEQUENCE: 6

Thr Leu Arg Gln His Asp Arg Leu
1               5

<210> SEQ ID NO 7
<211> LENGTH: 24
<212> TYPE: DNA
<213> ORGANISM: Artificial sequence
<220> FEATURE:
<223> OTHER INFORMATION: Synthesized: hspR mutation 3

<400> SEQUENCE: 7
ggcgcacgcc gctactgcct gcgc                                            24

<210> SEQ ID NO 8
<211> LENGTH: 8
<212> TYPE: PRT
<213> ORGANISM: Artificial sequence
<220> FEATURE:
<223> OTHER INFORMATION: Synthesized: hspR mutation 3

<400> SEQUENCE: 8

Gly Ala Arg Arg Tyr Cys Leu Arg
1               5

<210> SEQ ID NO 9
<211> LENGTH: 24
<212> TYPE: DNA
<213> ORGANISM: Artificial sequence
<220> FEATURE:
<223> OTHER INFORMATION: Synthesized: hspR mutation 4

<400> SEQUENCE: 9
ggcgcacgcc gctgctgcct gcgc                                            24

<210> SEQ ID NO 10
<211> LENGTH: 8
<212> TYPE: PRT
<213> ORGANISM: Artificial sequence
<220> FEATURE:
<223> OTHER INFORMATION: Synthesized: hspR mutation 4

<400> SEQUENCE: 10
```

```
Gly Ala Arg Arg Cys Cys Leu Arg
1               5

<210> SEQ ID NO 11
<211> LENGTH: 24
<212> TYPE: DNA
<213> ORGANISM: Artificial sequence
<220> FEATURE:
<223> OTHER INFORMATION: Synthesized: hspR mutation 5

<400> SEQUENCE: 11
ggcgcacgcc gccactgcct gcgc                                              24

<210> SEQ ID NO 12
<211> LENGTH: 8
<212> TYPE: PRT
<213> ORGANISM: Artificial sequence
<220> FEATURE:
<223> OTHER INFORMATION: Synthesized: hspR mutation 5

<400> SEQUENCE: 12

Gly Ala Arg Arg His Cys Leu Arg
1               5
```